US008780196B2

United States Patent
Vennewald

(10) Patent No.: US 8,780,196 B2
(45) Date of Patent: Jul. 15, 2014

(54) PARTICLE MEASURING INSTRUMENT, IN PARTICULAR FOR THE ANALYSIS OF GRAIN SIZES OF FINE AND VERY FINE BULK MATERIALS

(75) Inventor: Sven Vennewald, Oelde (DE)

(73) Assignee: Haver & Boecker OHG, Oelde (DE)

( * ) Notice: Subject to any disclaimer, the term of this patent is extended or adjusted under 35 U.S.C. 154(b) by 611 days.

(21) Appl. No.: 12/958,926

(22) Filed: Dec. 2, 2010

(65) Prior Publication Data
US 2011/0128375 A1 Jun. 2, 2011

(30) Foreign Application Priority Data

Dec. 2, 2009 (DE) .......................... 10 2009 056 503

(51) Int. Cl.
| H04N 7/18 | (2006.01) |
| G01N 1/20 | (2006.01) |
| B07B 1/42 | (2006.01) |
| G01N 15/02 | (2006.01) |
| G01N 21/85 | (2006.01) |
| G01N 21/84 | (2006.01) |
| G01N 15/14 | (2006.01) |

(52) U.S. Cl.
CPC ............ *G01N 1/20* (2013.01); *G01N 2015/025* (2013.01); *B07B 1/42* (2013.01); *G01N 2021/8592* (2013.01); *G01N 21/85* (2013.01); *G01N 15/0227* (2013.01); *G01N 2021/845* (2013.01); *G01N 2015/1497* (2013.01); *G01N 2015/0294* (2013.01); *G01N 15/1463* (2013.01)
USPC ................................ 348/135; 73/584; 427/600

(58) Field of Classification Search
CPC B05B 17/0607; B05B 17/0623; B05B 5/025; B07B 1/42; G01N 15/0227; G01N 2015/025; G01N 2015/1497; G01N 2021/845; G01N 2021/8592; G01N 21/85; G01N 15/1463; G01N 1/20; G01N 2015/0294
USPC .................... 118/627; 209/332, 365.1, 365.4; 239/102.2, 3, 703; 382/110, 141; 427/600; 348/135; 73/584
See application file for complete search history.

(56) References Cited

U.S. PATENT DOCUMENTS

| 3,198,170 A * | 8/1965 | Onishi ......................... 118/627 |
| 6,845,868 B1 * | 1/2005 | Krush et al. ............... 209/365.4 |
| 2004/0151360 A1 * | 8/2004 | Pirard et al. ................. 382/141 |
| 2005/0137078 A1 * | 6/2005 | Anderson et al. ............ 501/127 |

FOREIGN PATENT DOCUMENTS

| DE | 10 2006 049 517 A1 | 4/2008 |
| DE | 10 2007 033 629 A1 | 1/2009 |
| EP | 0 195 420 A2 | 9/1986 |
| WO | 2004/051237 A1 | 6/2004 |

* cited by examiner

*Primary Examiner* — Sath V Perungavoor
*Assistant Examiner* — Dakshesh Parikh
(74) *Attorney, Agent, or Firm* — Pearne & Gordon LLP

(57) ABSTRACT

Particle measuring instrument and method for the analysis of particles comprising a dosing device which dosing device can be set into vibrations by means of a vibration generator for conveying, while segregating, particles present in the dosing chute to at least one outlet of the dosing device. Other than a first vibration generator a second, different vibration generator is provided for segregating the particles present in the dosing device. The second vibration generator generates vibrations of a higher frequency compared to the first vibration generator.

18 Claims, 1 Drawing Sheet

Figure 1:
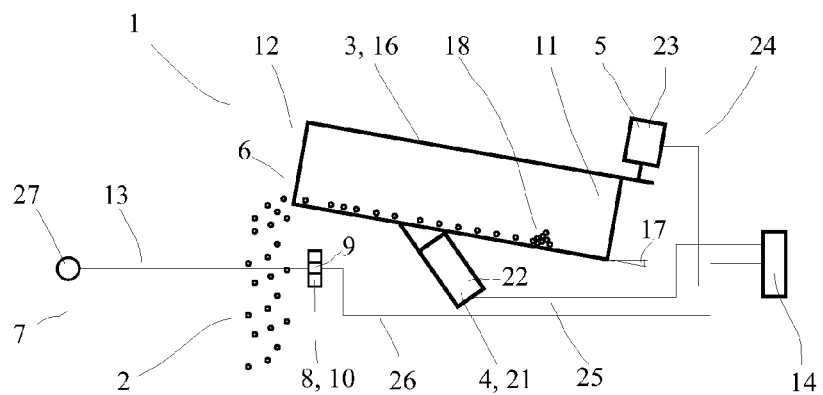

PARTICLE MEASURING INSTRUMENT, IN PARTICULAR FOR THE ANALYSIS OF GRAIN SIZES OF FINE AND VERY FINE BULK MATERIALS

The invention relates to a particle measuring instrument for the analysis of particles and in particular for the analysis of grain sizes of fine and very fine bulk materials.

For example in manufacturing sugar, coffee, and also in the field of the pharmaceutical industry or in manufacturing other bulk materials the grain size distribution of the particles is a significant parameter in production and in the application of the manufactured products. For example the dissolution rate of sugar particles in liquids depends on the grain size. Therefore the manufacturers of these bulk materials check the grain size distribution continuously or at regular intervals. To this end analysis samples are collected from the production and analyzed for their grain size distribution by means of specific particle analysis instruments.

In the prior art screen systems have become known among other things in which multiple series-connected screens of different mesh widths are employed to obtain a defined grain size distribution of the samples to be examined. It will, be determined what proportion by weight of the sample is still present on which screen.

Also, computer-aided analysis methods have become known in which the bulk materials to be examined are segregated and passed through the optical path of an optical analysis device. Images are taken during the free fall through the optical path and the particle sizes are detected and their statistic distribution determined, based on the shadow imaging on the sensor. A particularly significant factor in precision of measuring is to avoid as far as possible particle agglomerates because cohesive particles appear to be one joined particle in the optical path, thus resulting in determining too large grain sizes or length dimensions which would not be measured if the particles were entirely segregated.

Due to adhesive forces and cohesive forces and depending on the product to be examined the particles tend to adhere to one another more or less or else to bake onto the dosing device. If part of the sample remains in the dosing device the overall result determined will be incorrect since the detected grain size distribution only relates to the measured particles. Another drawback of caking in the dosing device is that in subsequent measurements such caking may be removed so as to render subsequent measuring results incorrect. One solution to this problem is cleaning the dosing device which, however, involves considerable additional work, thus decreasing cost effectiveness.

Against the background of the described prior art it is therefore the object of the present invention to provide a particle measuring instrument which allows increased precision by way of improved segregation of particles. Preferably, any baking to the dosing device is intended to be avoided or removed better.

This object is solved by the particle measuring instrument according to the invention having the features of claim 1. The method according to the invention is the subject of claim 11. Preferred more specific embodiments of the invention are indicated in the subclaims. Further advantages and characteristics of the invention can be taken from the embodiment.

The particle measuring instrument according to the invention for the analysis of particles is provided in particular for determining the grain size distribution of the particles of bulk materials and comprises at least one dosing device. The dosing device can be set into vibrations at least in part by means of a vibration generator for conveying, while segregating, particles present in the dosing device to at least one outlet of the dosing device. Other than the first vibration generator at least one second, different vibration generator is provided serving to further segregate the particles present in the dosing device. The second vibration generator is suitable and/or provided to generate vibrations of a higher frequency compared to the first vibration generator.

The particle measuring instrument according to the invention has many advantages. A considerable advantage of the particle measuring instrument according to the invention is that other than a vibration generator for conveying particles within the dosing device another vibration generator serving as a segregation device is employed. Employing two different vibration generators allows to achieve a clearly enhanced segregation which in turn allows to achieve increased precision of analysis results. Also, reproducibility increases considerably.

Preferably the particle measuring instrument comprises at least one analysis device having in particular at least one optical sensor device. The optical sensor device preferably comprises at least one camera line or one sensor line comprising a plurality of sensor elements. Preferably the signal of the sensor or camera line is captured at a high frequency. Particularly preferably the scanning frequency of the sensor line is in a range higher than 1000 Hz. In particularly preferred more specific embodiments the sensor line is scanned more than 10,000 times and in particular more than 20,000 times per second. In specific configurations the scanning frequency is approximately 40 or 60 MHz which, given a number of sensor elements of e.g. 2048 or 4096, results in a scanning frequency per sensor element between approximately 9 and 30 kHz. Such a high scanning frequency allows to determine a two-dimensional signal from a sensor signal that is actually one-dimensional since within the time interval from a first, determined signal to the second, scanned signal the positions of the particles have changed only slightly in a free fall through the optical measuring section so as to allow to precisely determine the shapes and sizes of each of the particles.

It is likewise possible to employ planar sensors to directly capture a complete image of the individual particles.

Different particle parameters such as particle size and particle shape can in particular be determined. Optionally the type of particle can be determined as well.

It is advantageous that the second vibration generator is suitable to generate vibrations of a higher frequency compared to the first vibration generator. The first vibration generator may substantially serve to convey the particles to the dosing device outlet while the second vibration generator due to its higher vibration frequency may contribute more to segregating the particles.

The first vibration generator is in particular suitable and intended to generate vibrations in the range between 10 Hz and 1,000 Hz, in particular between 10 Hz and 500 Hz. The vibration frequency of the first vibration generator may be derived from the frequency of the alternating current network (AC network). The central vibration frequency of the first vibration generator may for example correspond to the AC network frequency or may correspond to a (low) integer multiple of the AC network frequency.

The second vibration generator preferably has at least double and in particular at least ten times the central vibration frequency compared to the first vibration generator. The central vibration frequency of the second vibration generator is in particular in the range of higher than 1,000 Hz and preferably in the range of higher than 5,000 Hz and particularly preferably in the range of higher than 10,000 Hz. In a specific and advantageous configuration the second vibration generator is configured as an ultrasonic generator generating in particular frequencies between 30 and 40 kHz and preferably between 33 and 37 kHz.

The second vibration generator may be suitable and intended to generate a vibration frequency that is in particular variable over time The vibration frequency of the second vibration generator may in particular be periodically variable within specified and preferably adjustable frequencies. A changing vibration frequency in the second vibration generator for segregating the particles stimulates particle agglomerates and baking to the dosing device at different frequencies so as to allow a still better segregation of the particles from one another and better removing from the dosing device.

The formation of hot spots is basically already prevented due to the two vibration generators. These nodal points of vibration where particles are deposited permanently are prevented to a still larger degree by way of varying the vibration frequencies of the second and/or first vibration generator such that complete emptying of the dosing device is ensured as a rule.

The dosing device preferably comprises a dosing chute which, is closed at one of its ends and is approximately U-shaped with the dosing chute outlet being provided at the open end of the dosing chute.

The dosing device and in particular the dosing chute may be oriented at an adjustable angle to the horizontal. The dosing chute outlet may be arranged to lie higher or else lower than the closed end of the dosing chute. Depending on the angle setting a first vibration generator for conveying the particles may optionally be omitted.

Preferably at least one light source is provided emitting light to the sensor device and which may be configured for example as a CCD line or a CCD camera. The optical path between the light source and the sensor device is oriented such that particles falling down from the dosing device outlet cross the optical path. The high scanning frequency of he sensor device allows to ensure that each particle is reliably detected.

In all of the configurations a data processing device is preferably provided to record and analyze the signals captured by the sensor device. To this end the data processing device may comprise a volatile and in particular a permanent memory for storing the captured signals.

In preferred configurations a temperature-control device may be provided to control the temperature of and for example heat the dosing device to further support particle segregation in the case of moisture-sensitive products.

Another particle measuring instrument according to the invention again serves for the analysis of particles and in particular of bulk materials, comprising a dosing device which dosing device can be set into vibrations at least in part by means of a vibration generator for conveying, while segregating, particles present in the dosing device to at least one outlet of the dosing device. The vibration frequency or a central vibration frequency of the vibration generator is higher than 500 Hz and in particular higher than 1 kHz. Preferably the central vibration frequency of the vibration generator is higher than 5 kHz and it may particularly preferably lie in the ultrasonic range.

Such a particle measuring instrument has the considerable advantage that the high vibration frequency of the vibration generator also causes reliable particle segregation and reliable particle conveying. Reliable and reproducible measuring results may in particular be achieved with a suitable inclination of the dosing device to the horizontal. The inclination of the dosing device to the horizontal during measuring may optionally be adjustable for example for varying the conveying speed by way of varying the inclination of the dosing device toward the dosing device outlet.

The method according to the invention for the analysis of particles is carried out employing at least one dosing device to receive a sample to be analyzed. The particles in the dosing device are segregated by means of a vibration generator and conveyed toward at least one outlet of the dosing device.

The dosing device for segregating and conveying the particles is set into vibrations by means of a first vibration generator and by means of a second, different vibration generator wherein the second vibration generator is able to generate and/or generates a vibration of a higher frequency compared to the first vibration generator. The method according to the invention allows a reliable, reproducible, high precision measuring of the grain size distribution of particles in particular of fine and very fine bulk materials.

Preferably the second vibration generator is subjected to vibrations of a higher frequency compared to the first vibration generator. In preferred configurations of the method the second vibration generator may be engaged additionally in sections or as needed.

In all of the configurations of the method it is preferred for the amplitude and/or the frequency of the first vibration generator and/or the second vibration generator to be controlled. For example the amplitude and/or the frequency of the first vibration generator may be controlled in dependence on the optical density of the captured signal. The propulsion of the particles to be analyzed can in particular be increased automatically if the optical density is too low and it can be decreased—preferably automatically—if the number of the particles to be detected is too high at any time.

Further advantages and features of the present invention follow from the embodiment which will be explained below with reference to the enclosed figures.

Figure 2:
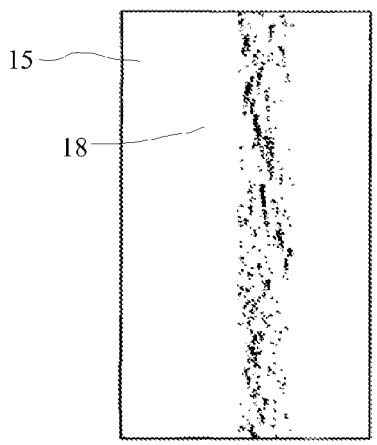
Figure 3:
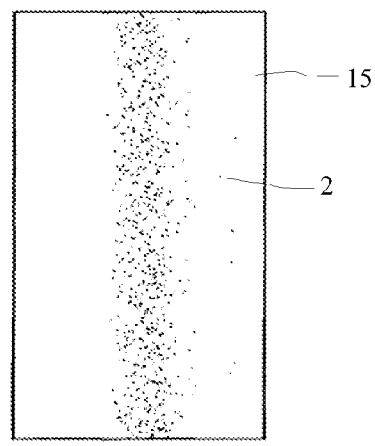

The figures show in:

FIG. 1 a schematic side view of a particle measuring instrument according to the invention;

FIG. 2 the signal of a sensor in the case of agglomerated particles;

FIG. 3 the sensor signal in the case of adequate segregation; and

Figure 4:
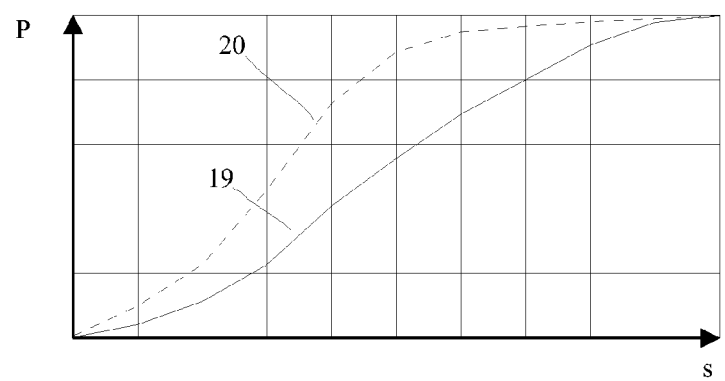

FIG. 4 the curve traces of the sensor signals with the ultrasonic generator activated and with the ultrasonic generator deactivated.

With reference to the FIGS. 1 to 4 an embodiment of the particle measuring instrument according to the invention will be described below.

The optical particle measuring instrument 1 illustrated in a simplistic, schematic side view in FIG. 1 serves for analyzing particles 2 in particular of fine and very fine bulk materials. Some individual particles 2 of the bulk material are schematically illustrated in FIG. 1.

The dosing device 3 of the particle measuring instrument 1 configured as a dosing chute 16 presently comprises a closed end 11 and an open end 12 at which the outlet 6 of the dosing chute 16 is provided.

Presently the dosing chute 16 is on the whole disposed under an angle 17 to the horizontal with the dosing device in the illustrated embodiment rising toward the outlet 6 such that in conveying out of the dosing chute 16 toward the outlet 6 the particles must overcome a certain height difference. In other preferred configurations the dosing chute 16 is disposed horizontally.

In the embodiment a first vibration generator 4 is provided as the drive device 21. The vibration generator 4 is presently configured as a magnetic drive 22 vibrating at a central vibration frequency derived from the vibration frequency of the public AC network.

The vibration generator 4 is in particular provided for an adjustable vibration amplitude to accelerate or decelerate the propulsion of the particles 2 as needed when the optical density of the detected signal 15 (compare the FIGS. 2 and 3) is too high or too low. A too high optical density involves the risk that due to shadow imaging and the like multiple particles are detected as one single particle so as to result in defective determination of its grain parameters and in particular the grain size and grain shape.

If the determination of the grain size and/or grain shape is defective in the case of a large number of particles, then the entire measurement is defective on the whole and may be worthless since in the production of many bulk materials it is imperative that the precise, specified grain sizes and/or grain shapes are obtained.

If the dosing chute 16 is provided with only one conventional magnetic drive 22 vibrating at a low-frequency vibration of for example 50 or 100 Hz, it may happen that goods, baked on the dosing chute 16 or particle agglomerations 18 are not dissolved but either remain adhered in the dosing chute 16 or else exit the outlet 6 of the dosing chute 16 as one entire agglomerate 18.

If an agglomerate 18 exits the dosing chute, passing through the optical path 13 of the optical analysis device 7, then an incorrect measuring result is obtained since the agglomerate is determined in total for its grain size and/or grain shape but not for the individual particles 2. If such an agglomerate remains sticking in the dosing chute then the dosing chute requires comprehensive cleaning after each measurement which considerably reduces cost effectiveness.

Also, the preceding measurement is not taken of the entire sample such that there is no or an incomplete representative result for the entire sample.

For performing the measurement a light source 27 is provided which may for example be provided as an LED line, aligning a scanning curtain by the linear CCD camera 10 or camera line 9. The camera line 9 is connected with the data processing device 14 via an electrical connection line 26.

Likewise the vibration generators 4 and 5 are connected with the data processing device 14 via electrical connection lines 25 and 24.

The light source 27 is also connected with the data processing device 14 and an energy source via corresponding lines, which are not shown.

The data processing device 14 controls the measuring process and in particular also controls the amplitude and if required the frequency of the vibration generator 4 which serves as a drive device 21 for conveying the particles 2.

As required and in particular when measuring fine-grained bulk materials the second vibration generator 5 is engaged additionally, presently configured as an ultrasonic generator generating vibrations in the double-digit kilohertz range. Due to the high-frequency vibration of the vibration generator 5 which may for example be connected with the dosing chute 16 of the dosing device 3 by a simple screw connection, the entire dosing device is set to high-frequency vibration causing any particle agglomerates and even persistently sticking baking 18 at the dosing chute 16 to dissolve and the particles 2 to be segregated to a considerably improved extent.

FIGS. 2 and 3 show the difference in measuring finely powdered bulk materials such as coffee or sugar with an additional vibration generator 5 engaged and disengaged. A repetition of the measurement illustrated in FIG. 3 with the same sample with the ultrasonic generator engaged will obtain the same measuring result.

While in FIG. 2 the plotted two-dimensional signal detects individual agglomerates 18, these agglomerates 18 are not recognizable in the signals plotted in FIG. 3. Regarding these two measurements it must in particular be pointed out that the same sample was measured wherein one can only recognize in the measurement illustrated in FIG. 3 that agglomerates 18 were present in the preceding measurement. Measuring only by conventional method fails to reliably detect these agglomerates, and a defective distribution of the grain parameters is determined.

This interrelationship is again shown more clearly in FIG. 4. The signal curves 19 and 20 of the measurements from FIG. 2 and FIG. 3 are plotted in FIG. 4.

FIG. 4 shows the cumulative proportion P (also called Q3) of the particles over the grain size S. The curve trace 20 according to the measurement according to FIG. 3 with the ultrasonic vibration generator engaged shows a clearly steeper increase of the cumulated particle quantity over the particle size, while the curve 19 of the measurement according to FIG. 2 with the ultrasonic vibration generator disengaged shows a clearly slower increase of the cumulative particle quantity over the particle size.

This means that with the ultrasonic vibration generator 5 disengaged, clearly larger particles are determined while a correct measurement results in a curve trace 20 comprising a visible and significant shift of the grain size distribution into the smaller range.

Reproducibility increases considerably. Another measurement of the sample on which the curve 20 is based with the ultrasonic generator engaged, leads—in the scope of dimensional accuracy—to the same result. This means that the measuring method reproducibly leads to the same, high-quality result.

Another significant advantage is the fact that the entire sample is measured. Any adhering particles are reliably removed from the dosing chute 16 by the ultrasonic generator.

On the whole the invention provides a particle measuring instrument which allows a clearly improved resolution and a clearly improved measuring result when determining the grain parameters (e.g. grain size distribution and grain shape distribution) of fine and very fine-grain bulk materials. Also, additional cleaning is avoided in many cases because any particles 2 adhering to the dosing chute 16 are also reliably removed therefrom.

List of Reference Numerals:

1 particle measuring instrument
2 particle
3 dosing device
4 vibration generator
5 vibration generator
6 outlet
7 analysis device
8 sensor device
9 camera line
10 CCD camera
11 closed end
12 open end
13 optical path
14 data processing device
15 signal
16 dosing chute
17 inclination angle
18 agglomerate 19 curve
20 curve
21 drive device
22 magnetic drive
23 segregation device
24 connection line
25 connection line
26 connection line
27 light source
P proportion
s size

The invention claimed is:

1. A particle measuring instrument for the analysis of particles comprising at least one substantially horizontally aligned dosing device which dosing device is set into vibrations at least in part by means of a first vibration generator for conveying while segregating the particles present in the dosing device substantially horizontally to at least one outlet of the dosing device, characterized in that other than a first vibration generator a second, different vibration generator is provided for further segregating the particles present in the dosing device wherein the second vibration generator is configured as an ultrasonic generator which is periodically adjustable within specified frequencies and is provided to generate vibrations of a higher frequency compared to the first vibration generator, whereby the entire dosing device is set to high-frequency vibration causing any particle agglomerates and persistently sticking baking at the dosing device to dissolve.

2. The particle measuring instrument according to claim 1, wherein at least one analysis device is provided comprising at least one optical sensor device.

3. The particle measuring instrument according to claim 1, wherein the first vibration generator can generate vibrations in the range between 10 Hz and 1000 Hz or wherein the vibration frequency of the first vibration generator is derived from the AC network frequency.

4. The particle measuring instrument according to claim 1, wherein the second vibration generator has at least double a central vibration frequency compared to the first vibration generator.

5. The particle measuring instrument according to claim 1, wherein at least the second vibration generator can generate a variable vibration frequency which is periodically adjustable within specified frequencies.

6. The particle measuring instrument according to claim 1, wherein the dosing device comprises a U-shaped dosing chute closed at one end wherein the outlet is provided at the open end of the dosing chute.

7. The particle measuring instrument according to claim 1, wherein at least one light source is provided emitting light to at least one CCD camera as a sensor device, with the optical path disposed such that particles falling down from the outlet of the dosing device cross the optical path.

8. The particle measuring instrument according to claim 7, wherein a data processing device is provided by means of which the signals captured by the sensor device can be captured and analyzed.

9. The particle measuring instrument according to claim 1, wherein a central vibration frequency of the second vibration generator is higher than 500 Hz.

10. A method for the analysis of particles using at least one substantially horizontally aligned dosing device for receiving a sample to be analyzed wherein the particles are segregated in the dosing device by means of a first vibration generator and conveyed substantially horizontally to at least one outlet of the dosing device, characterized in that for segregating and conveying the particles the dosing device is set into vibrations by means of a first vibration generator and a second, different vibration generator wherein the second vibration generator is configured as an ultrasonic generator which is periodically adjustable within specified frequencies and generates a vibration of a higher frequency compared to the first vibration generator, whereby the entire dosing device is set to high-frequency vibration causing any particle agglomerates and persistently sticking baking at the dosing device to dissolve.

11. The method according to claim 10, wherein the amplitude and/or the frequency of at least the first and/or the second vibration generator is controlled.

12. The method according to claim 10, wherein the second vibration generator is additionally engaged in sections.

13. The particle measuring instrument according to claim 1, wherein at least one analysis device is provided comprising at least one optical sensor device and at least one camera line.

14. The particle measuring instrument according to claim 1, wherein the first vibration generator can generate vibrations in the range between 10 Hz and 500 Hz.

15. The particle measuring instrument according to claim 1, wherein the second vibration generator has at least ten times a central vibration frequency compared to the first vibration generator.

16. The particle measuring instrument according to claim 1, wherein at least the second vibration generator can generate a variable vibration frequency which is periodically adjustable within specified and adjustable frequencies.

17. The particle measuring instrument according to claim 1, wherein a central vibration frequency of the second vibration generator is higher than 1 kHz.

18. The particle measuring instrument according to claim 1, wherein a central vibration frequency of the second vibration generator is higher than 5 kHz.

* * * * *